United States Patent [19]

Heyden

[11] Patent Number: 4,607,635

[45] Date of Patent: Aug. 26, 1986

[54] APPARATUS FOR INTUBATION

[76] Inventor: Eugene L. Heyden, S. 627 Bernard #8, Spokane, Wash. 99204

[21] Appl. No.: 655,089

[22] Filed: Sep. 27, 1984

[51] Int. Cl.⁴ .......................................... A61M 16/00
[52] U.S. Cl. ................... 128/207.15; 604/35; 604/43
[58] Field of Search ...................... 128/200.26, 207.15, 128/911, 207.14; 604/27, 35, 36, 41, 43, 45

[56]  References Cited

U.S. PATENT DOCUMENTS

| | | | |
|---|---|---|---|
| 1,188,180 | 6/1916 | Kells . | |
| 2,491,647 | 12/1949 | Colavita | 128/275 |
| 2,614,563 | 10/1952 | Devine, Jr. | 128/276 |
| 3,173,418 | 3/1965 | Baran | 128/351 |
| 3,322,126 | 5/1967 | Rusch et al. | 128/351 |
| 3,384,089 | 5/1968 | Shriner | 128/350 |
| 3,421,510 | 1/1969 | Kettenbach | 128/350 |
| 3,426,759 | 2/1969 | Smith | 128/350 |
| 3,683,908 | 8/1972 | Michael et al. | 128/145.7 |
| 3,771,527 | 11/1973 | Ruisi | 128/350 |
| 3,788,326 | 1/1974 | Jacobs | 128/207.15 |
| 3,902,492 | 9/1975 | Greenhalgh | 128/241 |
| 4,037,605 | 7/1977 | Firth | 128/207.15 |
| 4,090,518 | 5/1978 | Elam | 128/349 |
| 4,119,101 | 10/1978 | Igich | 128/351 |
| 4,156,428 | 5/1979 | Henkin | 128/207.15 |
| 4,166,468 | 9/1979 | Haynie | 128/351 |
| 4,168,699 | 9/1979 | Hauser | 128/768 |
| 4,275,724 | 6/1981 | Behrstock | 128/207 |
| 4,305,392 | 12/1981 | Chester | 128/276 |
| 4,316,459 | 8/1979 | Walski | 128/207.17 |
| 4,320,754 | 3/1982 | Watson et al. | 128/911 |
| 4,327,720 | 5/1982 | Bronson | 128/207.15 |
| 4,327,721 | 5/1982 | Goldin et al. | 128/207.15 |
| 4,405,308 | 9/1983 | Jessup | 604/200 |
| 4,435,174 | 3/1984 | Redmond et al. | 604/174 |
| 4,446,864 | 5/1984 | Watson | 128/207.14 |
| 4,449,563 | 5/1984 | Szachowicz et al. | 128/200.26 |
| 4,453,545 | 6/1984 | Inoue | 128/207.15 |
| 4,488,548 | 12/1984 | Agdanowski | 128/204.25 |
| 4,527,559 | 7/1985 | Roxburg et al. | 128/207.17 |

OTHER PUBLICATIONS

Arhelger, Tracheotomy and New Tracheal Tube, Surgery, Feb. 1951, pp. 260–266.
Advertising Sheet for NCC Division Mallinckrodt, Inc.'s "Hi–Lo Jet Tracheal Tube", NCC Division Mallinckrodt, Inc., Hook Road, Argyle, NY 12809.

Primary Examiner—Henry J. Recla

[57]    ABSTRACT

An endotracheal tube (18) is adapted to incorporate an elongated passage (40) along its length. Ports (48) are located along the elongated passage (40) and arranged to provide for removal of secretions that accumulate outside the endotraecheal tube and between the endotracheal tube and a substantial length of the intubated pathway wall (50) when the endotracheal tube is in place. The positioning of ports (48) is such that direct contact of the port openings with the mucosa is avoided, thereby minimizing blockage of these openings. The elongated passage provides a shield for a suction catheter (54) which is insertable into the elongated passage (40) and used to transport the secretions out of the intubated pathway. The suction catheter (54) is easily removed to allow for cleaning or replacement.

9 Claims, 6 Drawing Figures

4,607,635

APPARATUS FOR INTUBATION

BACKGROUND OF THE INVENTION

This invention relates to tubes or cannulae used for intubation within a body pathway, such as endotracheal, endobronchial, and tracheostomy tubes, and more particularly to such an apparatus having provision for removal of secretions that accumulate between the tube and the inner wall of the body pathway.

Representative of existing intubation apparatus are the endotracheal tubes of Chester, U.S. Pat. No. 4,305,392 and Goldin et al., U.S. Pat. No. 4,327,721. The typical use of endotracheal tubes is to promote a patient's respiration by providing for mechanical ventilation of a patient's lungs. Endotracheal tubes are usually cylindrical tubes which, when intubed, have a distal end residing within the trachea; the proximal end extending through the patient's mouth. A circumferentially extending inflatable cuff is positioned near the distal end of the tube and is inflated after intubation by way of an inflation lumen formed within the wall of the tube. The inflated cuff provides a seal between the tube and the tracheal walls which thereby allows oxygen or other gases to be forced into the lungs without escape through the mouth or nose of the patient.

Commonly, mucous secretions and other fluids accumulate along the intubated pathway above the inflated cuff. The amount of accumulations increases with the amount of time the endotracheal tube is in place. The patient may try to swallow the secretions, causing muscle contractions and tissue movement around the endotracheal tube, thereby contributing to the discomfort that is present during intubation. When the cuff is deflated accidentally or intentionally, such as prior to extubation, these accumulated secretions can enter the lower trachea and bronchi causing severe coughing and increasing the chance that the patient will contract pneumonia. Thus, a prime consideration in the use of any endotracheal tube is the efficient removal of accumulated secretions during intubation and especially just prior to extubation.

One method of removing these accumulated secretions is by inserting a suction catheter outside of and along the endotracheal tube between the tube and the wall of the intubated pathway. Such a procedure, however, results in irritation of the mucosa, stimulating the gag reflex of the patient. Furthermore, control of the suction catheter is difficult and thus it may be hard to avoid unintentional insertion of the suction catheter into the esophagus. As an attempt to remove secretions, the Chester patent shows the use of a suction chamber extending circumferentially around the endotracheal tube just above the cuff. Four ports are located about the periphery of the chamber, providing communication between the chamber and the area between the endotracheal tube and the tracheal wall. A lumen for suction of fluids extends from the suction chamber through the tube wall and out of the patient where it is connected with a suction source.

The positioning of the ports in Chester provides for removal of secretions directly above the cuff. However, secretions in a recumbent patient accumulate all along the endotracheal tube length above the cuff. Therefore, drainage ports located solely near the cuff would be inadequate to remove all of these accumulations. Furthermore, Chester and other prior art do not resolve the problem of occlusion of the suction lumen when blood clots, mucous plugs, or other obstructing material prevent removal of accumulations.

SUMMARY OF THE INVENTION

In its preferred form, the present invention provides an endotracheal tube that allows effective drainage of secretions that accumulate within the intubated pathway while the tube is in place. Specifically, a passage is incorporated into a standard endotracheal tube and used to guide movement of a suction catheter along the substantial length of the tube. The suction catheter is used to remove secretions at any of several locations along the entire intubated portion of the apparatus above the cuff. Drainage ports are arranged to eliminate the problem of occlusion or tissue entrapment that commonly occurs when such ports are placed in substantial contact with the tissue of the tracheal wall. Insertion and removal of a suction catheter is accomplished with no noxious stimulation of mucosa. The suction catheter can therefore be freely moved along the length of the endotracheal tube with no patient discomfort or harm. The easy insertion and removal of a suction catheter also provides for cleaning or replacement of the catheter should any blockage occur. Finally, the same passage may also be used for the insertion of other devices such as an intubation stylet or humidifying catheter with no discomfort to the patient.

BRIEF DESCRIPTION OF THE DRAWINGS

The invention can best be understood by referring to the following portion of the specification taken in conjunction with the accompanying drawings in which:

FIGS. 3 and 4 are enlarged cross-sectional views of the device;

DETAILED DESCRIPTION OF THE INVENTION

Figure 1:
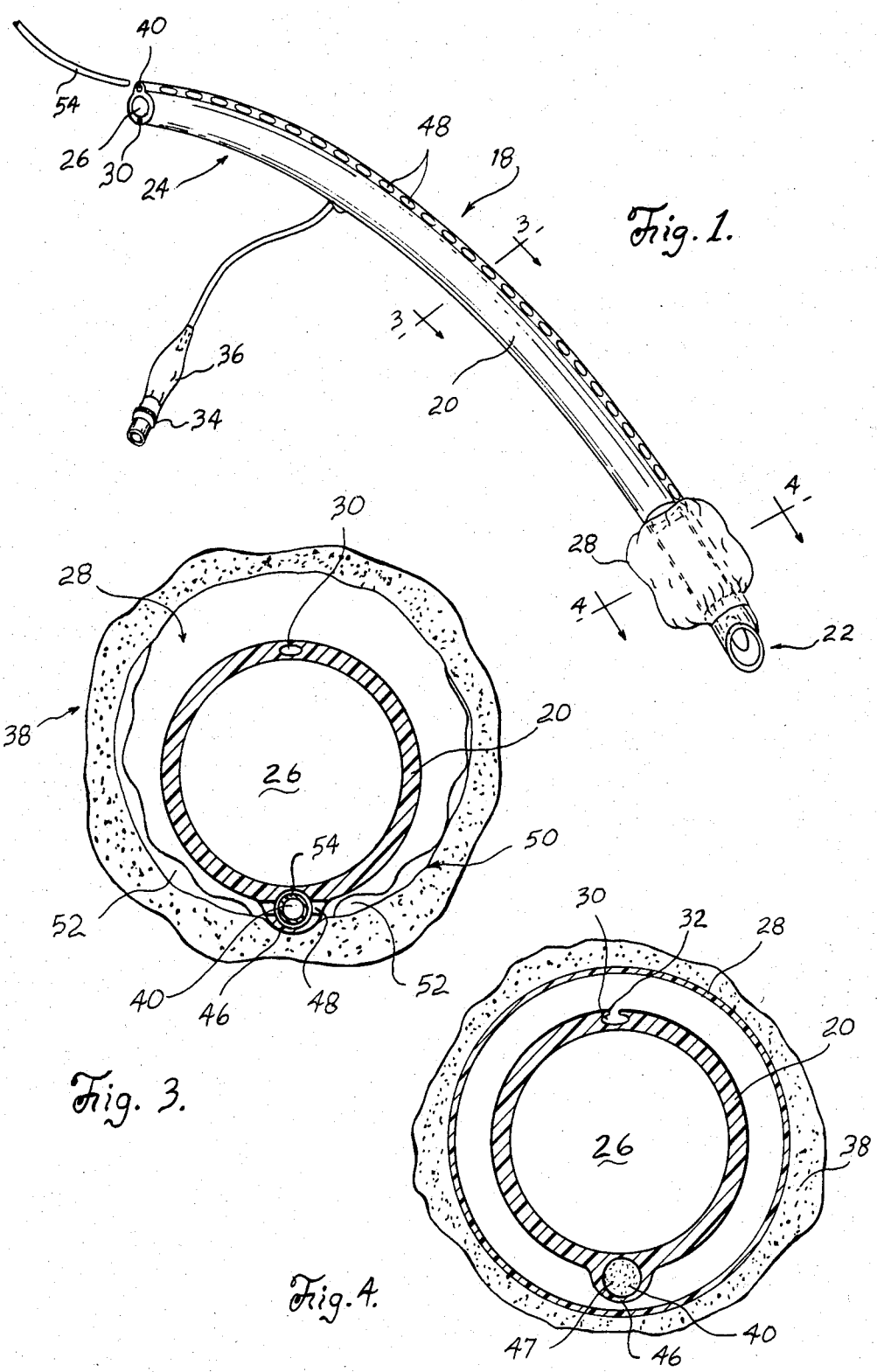
FIG. 1 is a pictorial illustration of the preferred embodiment of the invention.
Figure 2:
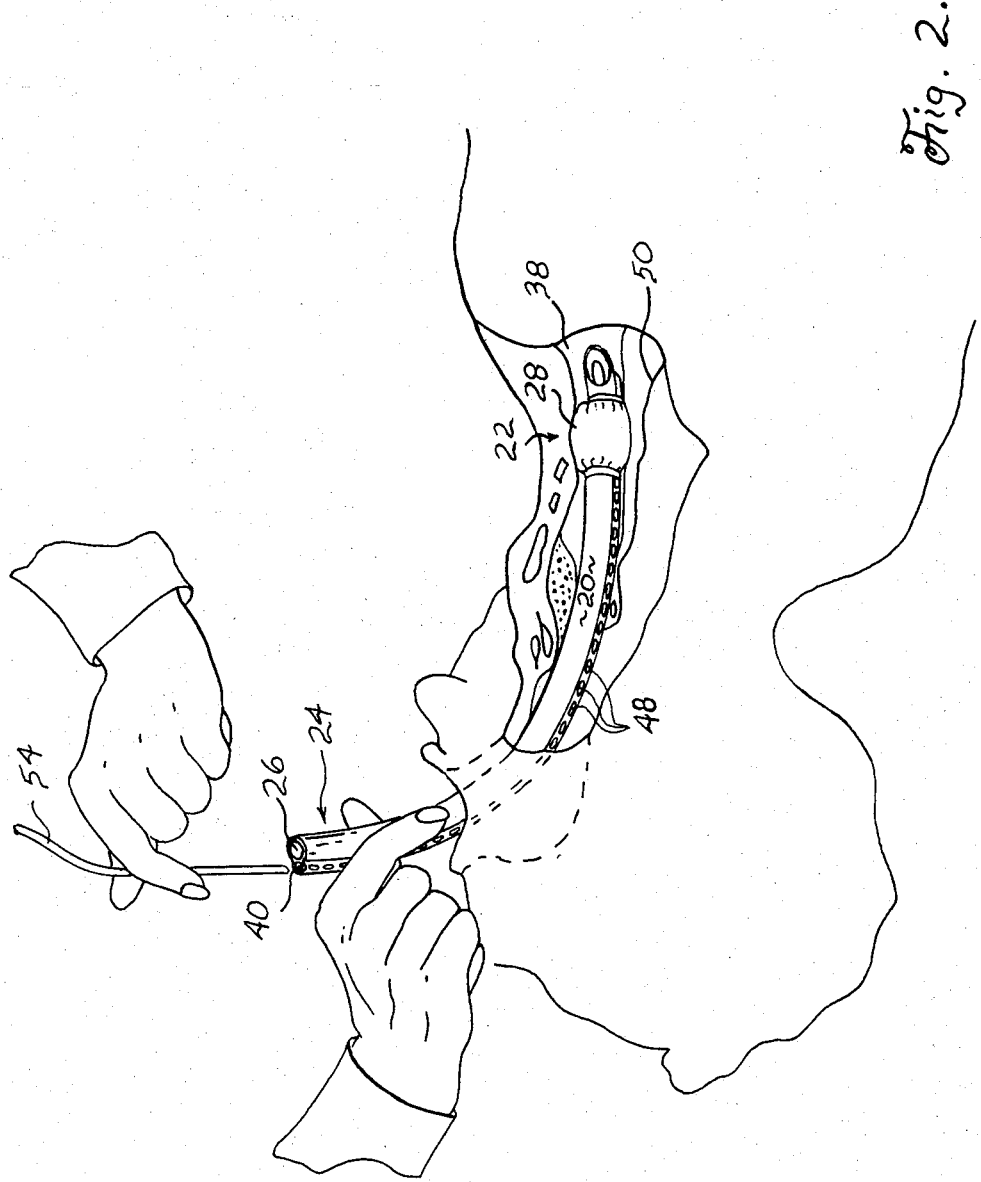
FIG. 2 illustrates the device intubed within the trachea of a recumbent patient.

With reference to FIGS. 1 and 2, the preferred embodiment of the endotracheal tube 18 includes a tubular member 20 having a distal end 22 and a proximal end 24. The tubular member is substantially cylindrically shaped in cross section and made of a resilient plastic material. The distal end 22 is inserted into the trachea 38. The proximal end 24 extends from the mouth or naris of the patient and is connectable with a suitable ventilating device (not shown). Between its distal and proximal ends, tubular member 20 has defined therein a continuous primary lumen 26.

An inflatable cuff 28 is attached around the circumference of the tubular member 20 near its distal end. An inflation lumen 30 is formed within the wall of the tubular member and terminates at one end at a point, on the distal end of the tubular member, that is enveloped by cuff 28. Inflation ports 32 FIG. 4) located near the distal end of the inflation lumen 30 provide communication between the inflation lumen and the interior portion of the cuff 28. The proximal end of the inflation lumen 30 is attached to a check valve 34 and test balloon 36. When the endotracheal tube 18 is properly located within a patient, the check valve 34 is connected to a suitable inflation source (not shown). The cuff 28 is then inflated with the test balloon 36 giving an external indication of the cuff's inflated condition. The inflated cuff 28 acts to confine, to the primary lumen 26 of the endotracheal tube, all passage of respiration gases between the lungs and the ventilation device while preventing material from entering the patient's lungs from the upper airway. This sealing function of the cuff is crucial to proper mechanical ventilation and protection of the lower airway.

Referring most particularly to FIGS. 1, 3 and 4, the preferred embodiment of this invention has an elongated passage 40 integrally formed within the wall of the tubular member 20. The elongated passage 40 is substantially circular in cross section and extends the length of the tubular member 20 between its proximal and distal ends. In the preferred embodiment, the distal end of the elongated passage is occluded. As shown in the cross section of FIG. 4, a portion of the elongated passage 40 that is near the distal end 22 of the endotracheal tube is filled with radiopaque material 47 for the purpose of radiographic determination of correct endotracheal tube placement.

As noted earlier, the elongated passage 40 is integrally formed within the wall of the tubular member 20. Furthermore, the cross-sectional diameter of the elongated passage 40 is larger than the thickness of the wall of the tubular member 20. The central axis of the elongated passage 40 is radially offset at a distance from the central axis of the tubular member 20 such that the additional thickness in the wall of the tubular member that is caused by the integrally formed elongated passage projects outwardly from the internal wall of tubular member 20. That is, the elongated passage 40 forms an outward protrusion 46 in the outer wall of tubular member 20 that extends along the substantial length of the tubular member.

The normal shape of the endotracheal tube is arcuate and, when it is intubed within a recumbent patient, the convex outer portion of the tube is positioned downwardly. The protrusion 46 of the tubular member 20 is located along the convex outer portion of the endotracheal tube and therefore positioned along the lowest portion of the pathway wall 50. Ports 48 are positioned at spaced-apart locations along the length of the protrusion 46. As shown in FIG. 3, the portion of the protrusion 46 that is radially most distant from the center of the tubular member remains intact; the ports 48 placed away from this portion. The significance of the position of the ports can be appreciated by close scrutiny of FIG. 3. Specifically, gravitational forces cause secretions 52 to accumulate in the lowest portion of the pathway wall 50. Ports 48 provide communication of these secretions through the protrusion 46 into the elongated passage 40. Thus, when a suction catheter 54 is inserted into the elongated passage, the secretions 52 can pass through ports 48 and out through the suction catheter. During intubation of a recumbent patient, the radially most distant portion of the protrusion 46 will rest upon the lowest portion of the pathway wall 50. Since the ports 48 are placed away from this portion of the protrusion and thus not in direct contact with the pathway wall, the ports will not irritate nor become blocked by the mucosal lining. Draining of secretions 52 can therefore be most effectively accompllished by this arrangement. Positioning the protrusion 46 and ports 48 along the convex outer portion of the tube also eliminates any interference with, or possible damage to, the vocal cords. That is, the protruding portion 46 will be located away from the region of the cords when the endotracheal tube is properly positioned in the trachea 38.

Another important characteristic of the ports' positions is that they extend between the cuff 28 and the proximal end 24 of the elongated passage 40. Thus, when a device such as suction catheter 54 is inserted into the elongated passage, suction can be effectively applied at a wide range of points along the intubated pathway by controlling the length of the inserted catheter. The catheter can also be held stationary at certain points along the elongated passage for continuous treatment of an area such as a bleeding site. Also, the catheter 54 can be extended to a point very near the cuff 28 where secretion removal is absolutely necessary for good patient care. It is not necessary, however, that ports 48 be placed continuously along the entire length of the elongated passage 40 as illustrated in the drawings, and the ports may be placed only at those locations where access is desired from the elongated passage 40 to the intubated pathway for the purposes of secretion removal, irrigation, or the like. It can be appreciated that the movement of the suction catheter 54 will not appreciably contact the wall of the intubated pathway since the suction catheter is substantially shielded from such contact while residing within the elongated passage 40. Should the suction catheter 54 become plugged or otherwise inoperable it can be removed and replaced at any time with no noxious stimulation of a wall of the intubated pathway.

It can also be appreciated that when suction catheter 54 is removed from the elongated passage 40, various irrigation or humidifying treatments can be applied with catheters inserted into the elongated passage. The elongated passage 40 can also accomodate other instruments such as an intubation stylet to strengthen or adjust the curvature of the endotracheal tube. Thus, there is no need to use the primary lumen 26 (at the risk of introducing contaminants therein) to house the intubation stylet. If the elongated passage 40 is used solely for this latter purpose, the ports 48 of the preferred embodiment are not necessary.

Figure 5:
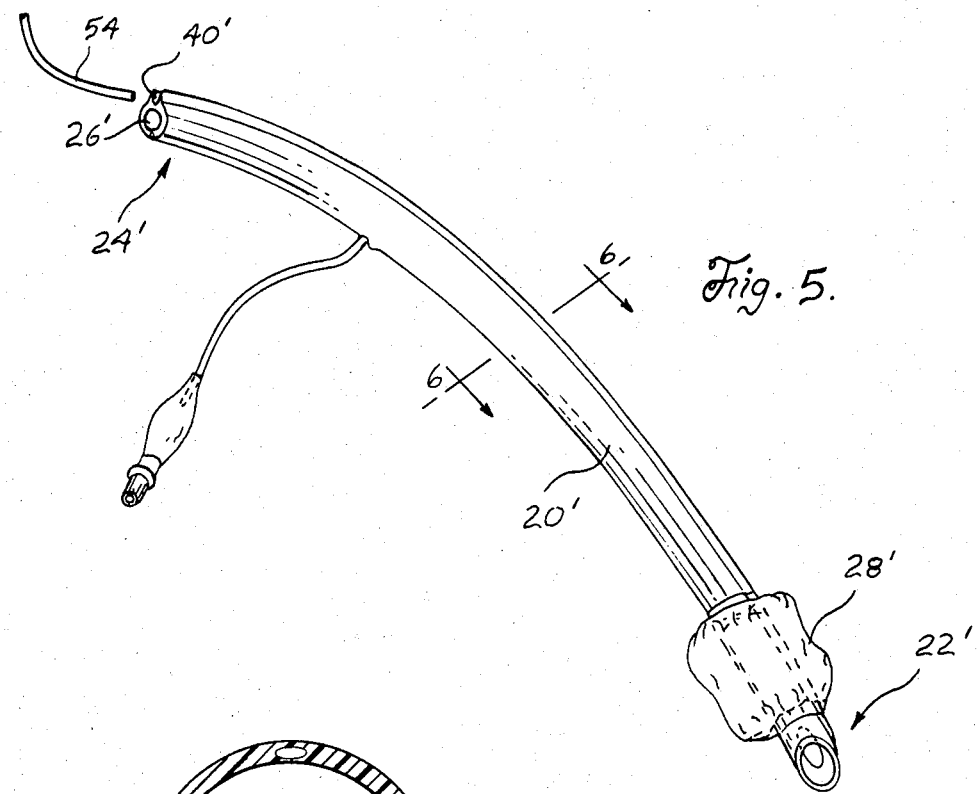
FIG. 5 is an illustration of an alternative embodiment.
Figure 6:
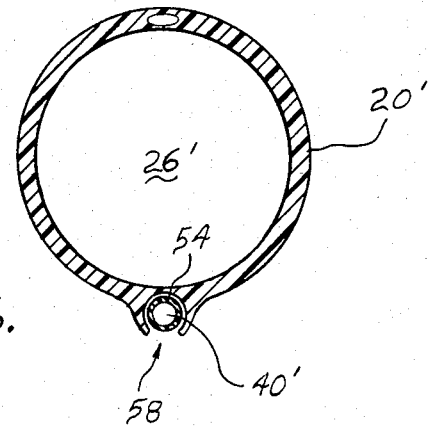
FIG. 6 is an enlarged cross-sectional view of the alternative embodiment of FIG. 5.

An alternative embodiment is shown in FIGS. 5 and 6, whereby the elongated passage 40' is substantially positioned within the tubular member 20' as the elongated passage 40 of the preferred embodiment. No ports are present in this embodiment; instead a longitudinal slit 58 extends along the length of the tubular member from the proximal end 24' to a point near the cuff 28' whereby a suction catheter 54' can be guided down the elongated passage 40' for removal of secretions at any point along the length of the elongated passage above the cuff 28'.

As in the preferred embodiment, the elongated passage 40' of the alternative embodiment is occluded at its distal end to prevent the escape of respiratory gases therethrough and to prevent passage of the catheter 54 beyond the distal end of the endotracheal tube.

Although the previous discussion has been devoted to the use of the invention as embodied in an endotracheal tube, it is pointed out that the features of the invention are also applicable to use in other cannulae such as endobronchial or tracheostomy tubes. Thus, while the invention has been described with reference to a preferred embodiment it is clearly understood by those skilled in the art that the invention is not limited thereto. Rather, the scope of the invention is to be interpreted only in conjunction with the appended claims.

The embodiments of the invention in which an exclusive property or privilege is claimed are defined as follows:

1. An apparatus for intubation of a body pathway, comprising:

an elongated tubular member having a wall with an inner wall surface and an outer wall surface, and also having a central axis, said tubular member having a distal end residing within the body pathway during intubation, and a proximal end extending from the body pathway during intubation;

a primary lumen defined by the wall of said tubular member and extending from said distal end to said proximal end thereof;

an expandable cuff carried by said tubular member adjacent said distal end for providing, when expanded, a seal with walls of the body pathway;

an elongated guide means adapted for slidably receiving a suction catheter therein and having a region therein for accommodating said suction catheter, said guide means integral with and defined within the wall of said tubular member, having a portion thereof included in the vicinity of the proximal end of said tubular member, and extending in length therein sufficiently to provide travel by said suction catheter away from a proximal end thereof along a substantial length of said tubular member toward an opposing distal end thereof located in the vicinity of said end toward cuff while preventing said suction catheter from contacting a wall of said body pathway;

said guide means including fluid communication means integral to the wall of said tubular member and residing between the proximal end thereof and said cuff, said fluid communication means for providing fluid communication and fluid transport over a substantial length of said guide means between the region within said guide means and the body pathway whereby said suction catheter can be moved within said guide means to remove secretions over any of several locations along a substantial length of said tubular member; and means to prevent the extention of said suction catheter from within said guide means to beyond the distal end thereof, preventing said suction catheter from advancing from said region to beyond said guide means.

2. The apparatus of claim 1, wherein said guide means includes an elongated passage defining said region for the accommodation of said suction catheter, said passage integrally formed within the wall of said tubular member and having an inner wall portion and an outer wall portion, said fluid communication means being formed in said outer wall portion.

3. The apparatus of claim 2, wherein said passage is formed within the wall of said tubular member and between the inner and outer wall surfaces thereof; and said fluid communication means is a plurality of ports formed in the wall portion of said passage at spaced-apart locations leading from the outer wall surface of said tubular member to the region defined by said passage.

4. The apparatus of claim 3, wherein the outer wall portion of said passage protrudes radially outward from the central axis of said tubular member, said protruding outer wall portion having an outermost portion being radially most distant from the central axis of said tubular member, said ports being located away from said outermost portion.

5. The apparatus of claim 4, wherein said tubular member is formed of resilient material being arcuately shaped in the relaxed state, said tubular member thereby having a convex side and a concave side, said protruding wall portion of said passage located on the convex side of said tubular member.

6. The apparatus of claim 2, wherein said passage is formed within the wall of said tubular member between the inner and outer wall surfaces thereof; and said fluid communication means includes an elongated slit formed in the outer wall portion of said passage leading from the outer wall surface of said tubular member to the region defined by said passage.

7. The apparatus of claim 6, wherein the outer wall portion of said passage protrudes radially outward from the central axis of said tubular member.

8. The apparatus of claim 7, wherein said tubular member is formed of resilient material being arcuately shaped in the relaxed state, said tubular member thereby having a convex side and a concave side, said protruding wall portion of said passage located on the convex side of said tubular member.

9. The apparatus of claim 1, wherein said means to prevent the extention of said suction catheter beyond said guide means includes a radiopaque material occlusively disposed within the region defined by said guide means, said radiopaque material residing in the vicinity of said distal end.

* * * * *